United States Patent
Zabret

(10) Patent No.: US 9,050,215 B2
(45) Date of Patent: Jun. 9, 2015

(54) HYGIENIC TAMPON, OPTIONALLY A DIGITAL OR APPLICATOR TAMPON, AS WELL AS APPARATUS AND METHOD FOR MANUFACTURING THEREOF

(75) Inventor: Andrej Zabret, Komenda (SI)

(73) Assignee: Tosama Tovarna Sanitetnega Materiala D.D., Domzale (SI)

( * ) Notice: Subject to any disclaimer, the term of this patent is extended or adjusted under 35 U.S.C. 154(b) by 684 days.

(21) Appl. No.: 13/377,202

(22) PCT Filed: Aug. 20, 2009

(86) PCT No.: PCT/SI2009/000035
§ 371 (c)(1),
(2), (4) Date: Feb. 1, 2012

(87) PCT Pub. No.: WO2010/144061
PCT Pub. Date: Dec. 16, 2010

(65) Prior Publication Data
US 2012/0130335 A1 May 24, 2012

(30) Foreign Application Priority Data

Jun. 12, 2009 (SI) .................................. 200900164
Aug. 19, 2009 (SI) .................................. 200900227

(51) Int. Cl.
*A61F 13/20* (2006.01)

(52) U.S. Cl.
CPC ......... *A61F 13/2051* (2013.01); *A61F 13/2082* (2013.01)

(58) Field of Classification Search
CPC ............ A61F 13/2034; A61F 13/2091; A61F 13/2031; A61F 2013/4587; A61F 13/2051; A61F 13/2082

USPC ............... 28/118–120, 128, 129; 604/385.18, 604/904, 385.17
See application file for complete search history.

(56) References Cited

U.S. PATENT DOCUMENTS 2,386,590 A * 10/1945 Calhoun .......................... 604/15
3,306,295 A * 2/1967 Penksa ..................... 604/385.18
(Continued)

FOREIGN PATENT DOCUMENTS

EP 0422660 4/1991
EP 0611562 8/1994
(Continued)

OTHER PUBLICATIONS

International Search Report, Dated Jan. 26, 2010; 7 pages, PCT/SI2009/000035, European Patent Office.

*Primary Examiner* — Tan-Uyen (Jackie) T Ho
*Assistant Examiner* — Peter S Vasat
(74) *Attorney, Agent, or Firm* — Haynes and Boone, LLP; William B. Nash; Joseph R. Mencher

(57) ABSTRACT

Hygienic tampon (1) consisting of absorbent fibrous material on the basis of natural and/or artificial fibers of each desired structure, which is formed into at least approximately cylindrical blank (10), which is symmetric with regard to a longitudinal axis (100) defining a direction of inserting the tampon (1) into each desired cavity of a human body. Such tampon (1) comprises four pairs of grooves (11, 12, 13, 14, 15, 16, 17, 18), which are equidistantly arranged in the circumferential direction of the tampon (1). Two pairs of grooves (11, 13, 15, 17) having a pre-determined width (B1) and depth (T1) are pressed in two planes being perpendicular to each other and coincide with the longitudinal axis (100). The other pairs of grooves (12, 14, 16, 18) having a pre-determined width (B2) and depth (T2) are pressed in two planes, which are perpendicular to each other and coincide with the longitudinal axis (100) under 45° with respect to previously mentioned planes.

20 Claims, 3 Drawing Sheets

(56) References Cited

U.S. PATENT DOCUMENTS 4,755,166 A 7/1988 Olmstead
6,310,269 B1 * 10/2001 Friese et al. .................. 604/379

FOREIGN PATENT DOCUMENTS

EP 1547555 6/2005
WO WO 2005/077312 A1 8/2005

* cited by examiner

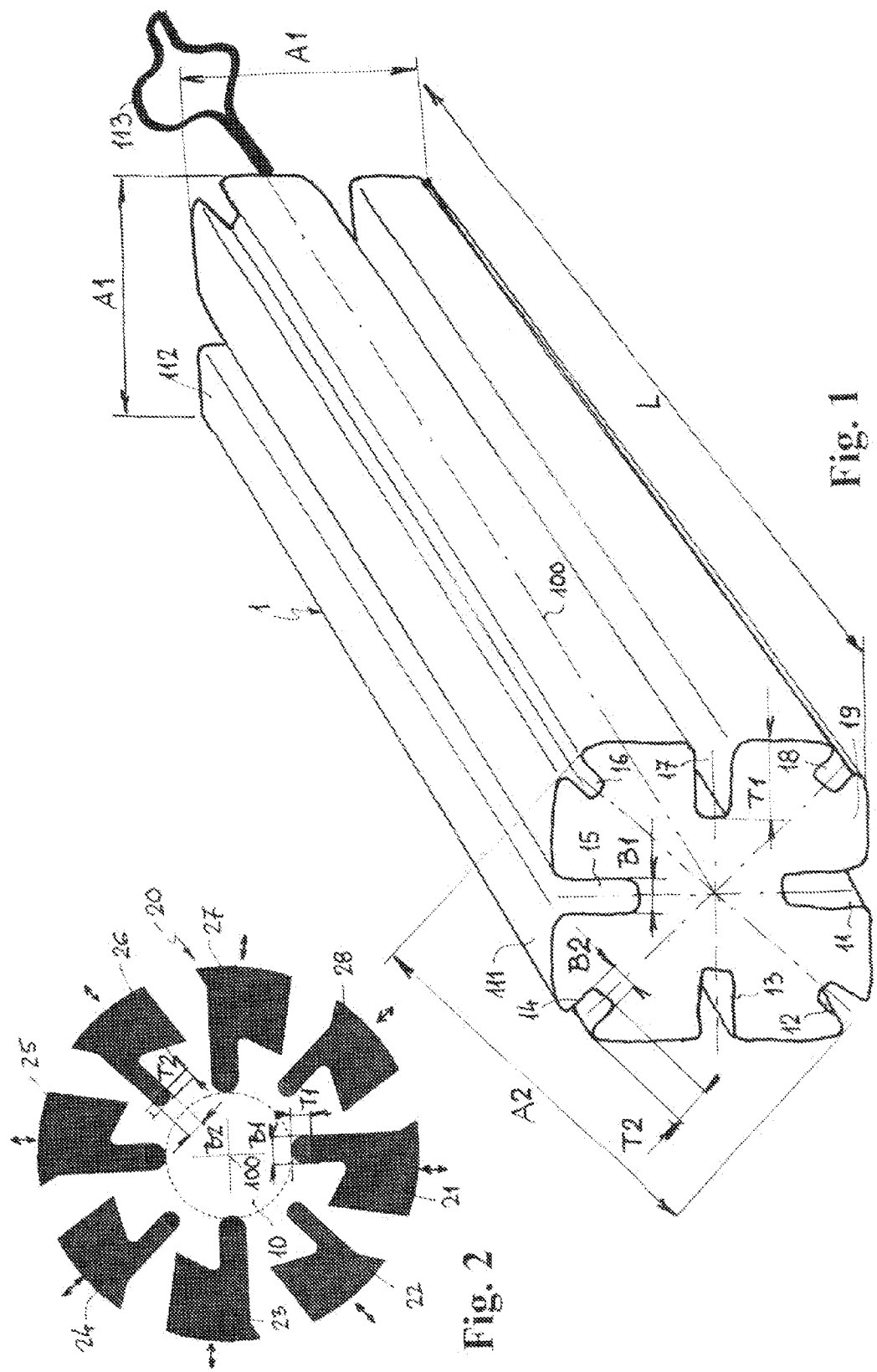

HYGIENIC TAMPON, OPTIONALLY A DIGITAL OR APPLICATOR TAMPON, AS WELL AS APPARATUS AND METHOD FOR MANUFACTURING THEREOF

CROSS-REFERENCE TO RELATED APPLICATION

The present application is a U.S. national-stage patent application of international patent application PCT/SI2009/000035, filed Aug. 20, 2009, which claims priority to Slovenia Patent Application No. P-200900164, filed Jun. 12, 2009 and Slovenia Patent Application No. P-200900227, filed Aug. 19, 2009, the disclosures of each of which are incorporated herein by reference in their entirety.

BACKGROUND

The present invention relates to a tampon, in particular to a hygienic tampon. Pursuant to the International Patent Classification, such inventions belong to medicine and hygiene, namely to tampons, in particular to menstrual hygienic tampons and corresponding accessories.

BRIEF DESCRIPTION OF DRAWINGS

FIG. 1 is a perspective view illustrating an embodiment of a tampon.

FIG. 2 is a cross-sectional view illustrating an embodiment of a tampon.

DESCRIPTION

Figure 3:
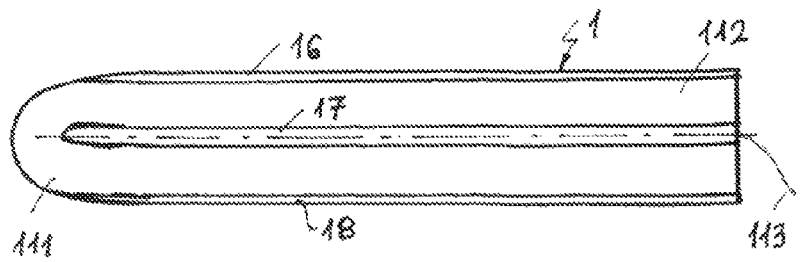
FIGS. 3-6 are side views illustrating embodiments of a tampon.

The purpose of the invention is to create a tampon, which could consist of the same raw materials and could be manufactured on the same machines and by means of the same operations as commercially interesting known tampons, wherein the stability of such tampon, namely a bending and buckling strength, would have to be as high as possible, and wherein upon exposing such tampon to moisture the shape thereof should change gradually and in appropriate manner, so that the absorbing capacity would have to be at least equal or even higher than by the known tampons, and penetration of liquid in the longitudinal direction of the tampon should be sufficiently decelerated in order to reduce the probability of leakage of said liquid out from a completely saturated tampon.

A tampon is disclosed in EP 0 422 660, which consists of a non-woven fibrous blank, which is formed by winding up a non-woven fibrous tape around the longitudinal axis, unless at least approximately cylindrical blank is obtained, which is then radially pressed by means of adequate pressing jaws, e.g. by means of a pressing device according to DE 19, 825 877, formed into a desired tampon. Such a tampon is generally still available in a cylindrical form, although grooves are formed on its external surface, which are directed radially inwards and extend in the longitudinal direction along said external surface of the tampon i.e. parallel with respect to the longitudinal i.e. the central axis of the tampon. Such tampons are known to those skilled in the art as "digital" tampons. A rib is available between each two neighboring grooves, by which the circumferential surface of said ribs determines the outer diameter of such tampon, and the bottom surfaces of said grooves determine the diameter of relatively high-compressed core of such tampon. Due to smooth subsequently compression of such tampon just in the area of said ribs, each available lateral surfaces of each rib become convex i.e. sloped, and the corresponding lateral surfaces of each two neighboring ribs are brought into mutual contact, by which a tubular space is formed adjacent to said compressed core, which extend parallel to the longitudinal axis of the tampon. Such structure should result in certain benefits, namely increasing of buckling strength and in particular also increasing of specific absorption including increasing of absorption rate in the longitudinal direction of the tampon. Stability of the tampon is of great importance when bearing in mind entrusting from the side of each user, which is quite important whenever the tampon is inserted. Although in the above cited document the absorption rate is declared as an important feature.

It is actually completely disregarded by each user, since some other features appear to be much more important during the practical use of such products. Accordingly, specific absorption seems to be quite important, which means each quantity of liquid, which can be absorbed by each tampon, by which also the weight of the tampon needs to be taken into account, and moreover also the wax, how the tampon is transformed upon being exposed to the moisture. As soon as appropriate end portion of the tampon according to EP 0 422 660 is exposed to the moisture, said end portion is capable to receive a relatively high quantity of liquid in a relatively short time period, by which said end portion of the tampon is then quickly expanding and becomes trumpet-like widened. Consequently, whenever some greater amount of the liquid needs to be absorbed, for example in the case of intensive menstruation, some leakage of previously absorbed liquid may easily occur from such quickly expanded end portion.

In addition to aid tampon, EP 0 422 660 also discloses a device and a process for manufacturing tampons of previously described art. Process of manufacturing has been roughly disclosed by means of description of concept and structure of the tampon as such, while a corresponding apparatus in addition to radial pressing jaws for forming grooves also includes appropriate means for subsequently applying each required pressure towards the circumferential surfaces of the ribs, wherein said means is preferably a conical die, through which the tampon is forwarded upon the ribs and grooves have already been formed thereon. However, applying such process should normally lead to obtaining a product with the previously identified deficiencies.

In order to further improve the absorption capacity, a tampon has been developed, which is disclosed in WO 01/075357 A3 and which is generally obtained from the same blank consisting of the same raw material like previously described tampon, wherein on the external surface of such tampon appropriate grooves and ribs are formed in practically the same manner i.e. by means of radial compression. However, in this case the ribs are not formed in the longitudinal direction of the tampon, but extend helically i.e. in the form of a helix under a relatively small angle relatively to the longitudinal axis of the tampon. Thanks to such approach, the overall length of ribs and grooves is correspondingly increased, by which the probability of leakage should be adequately reduced. However, manufacturing such tampon requires much more comprehensive technology when compared with technology of manufacturing tampons with ribs and grooves, which extend parallel with respect to the longitudinal axis of the tampon.

Moreover, the so-called tampon applicators are also known in the field of packaging and inserting such tampons.

A classic applicator, which is described e.g. in U.S. Pat. No. 3,643,661, consisting of a tampon inserted within an outer tube, into which an inner tube is inserted, which is—when observed in the direction of inserting the tampon—located behind of said tampon, wherein the outer diameter of said inner tube essentially corresponds to the inner diameter of the outer tube, so that by displacing said inner tube in the direction towards the tampon the last is pushed outwards from the outer tube and inserted or otherwise placed into each desired position. Essential length of such tampon is deemed to present the main deficiency of such applicators.

Recently developed applicators, so called "compact" applicators are essentially. shorter and much more comfortable, consisting thereby analogously of an inner tube inserted within an outer tube, as well as of a tampon, which is in its original position inserted within the inner tube and is—like e.g. in the applicator with a digital tampon according to EP 1 704 841 or in applicator with classic compressed tampon without ribs and grooves on the external surface according to U.S. Pat. No. 4,479,791—maintained in such position by means of retaining means, which are located within the outer tube in the vicinity of the inserting end portion thereof. When the inner tube is displaced in a direction away from said inserting end portion, the tampon remains in its position thanks to the above mentioned retaining means, by which the tampon is moved outwards from the inside area of the inner tube in order to remain stored within the outer tube. During the subsequent displacement of the inner tube towards the tampon i.e. towards the inserting end portion, the inner tube is rest onto the tampon in order to push it outwards from the interior of the outer tube. In order to improve cooperation between the tampon and said retaining means, the tampon is furnished on its inserting end portion with a mushroom-like or rivet-like head. Such tampon is e.g. disclosed in EP 0 355 396. In certain other cases, where said retaining and extracting of tampon is enabled in some different manner (like e.g. according to U.S. Pat. No. 4,291,694), forming such head on the tampon may also be avoided.

It is therefore obvious that such tampons, which may however practically also be used as digital tampons without the applicator, are used as applicator tampons and represent as such a part of the applicator or the applicator assembly, but are within the context of the present invention exposed to the same problems and to the same inventive concept, by which anyone of arising problems is then resolved.

The present invention on the one hand refers to a hygienic tampon, optionally a digital or applicator tampon, which consists of absorbent non-woven fibrous material on the basis of natural or synthetic fibers of each desired structure and is formed into a cylindrical blank. Such a tampon is preferably formed symmetrically with respect to the longitudinal axis, which extends in a direction of inserting tampon to each desired location, in particular into a cavity of the human body. For the purposes of easier inserting, such tampon preferably comprises appropriately adapted inserting end portion, whilst the opposite end portion is furnished with preferably non-removable string. Moreover, at least approximately in the longitudinal direction of the tampon i.e. at least approximately parallel with regard to the longitudinal axis extending grooves are formed on the external surface of the tampon, which are equidistantly spaced apart from each other in the circumferential direction of the tampon, so that between each two neighboring grooves there is a rib, which comprises an external surface, by means of which as well as by means of the external surface of each opposite rib with regard to the silhouette of the tampon the cross-section thereof, a transversal dimension of the tampon then is defined, while on the other hand the compressed core of the tampon, which consists of an absorbent fibrous material, is defined by means of appropriate bottom surfaces of said grooves.

The tampon according to the invention comprising four pairs of equidistantly spaced grooves arranged on its external surface, where two pairs of grooves having appropriately pre-determined width B1 and being pressed up to appropriately pre-determined depth T1 are arranged in two planes, which extend perpendicularly with respect to each other and throughout the longitudinal axis of the blank, while the other two pairs of grooves having appropriately pre-determined width B2 and being pressed up to appropriately pre-determined depth T2 are arranged in another two planes, which also extend perpendicularly with respect to each other and throughout the longitudinal axis of the blank, but are rotated for 45° around said longitudinal axis relatively to the planes of the previously mentioned groves, wherein each width B1, B2 and each depth T1, T2 of pressed grooves is determined in such a manner that the shape of the silhouette or of the cross-section of such obtained tampon essentially corresponds to a flattened circle or to a rounded square having rounded corner areas, by which the distance between each two opposite corner areas on the external surface of the tampon is for approx. 10 to 35% greater than the distance between each two opposite lateral areas on the external surface of the tampon.

In this, each width B1, B2 and each depth T1, T2 of such pressed grooves is determined in such a manner that either the following condition is fulfilled $$T1 \neq T2 \text{ and } B1 = B2,$$

or that $$T1 \neq T2 \text{ and } B1 > B2,$$

or optionally that $$T1 \neq T2 \text{ and } B1 < B2.$$

An embodiment of the tampon is foreseen, in which all grooves extend along the complete of the length of the tampon, while in another possible embodiment at least four grooves having the same width and the same depth extend along the complete length of the tampon.

Furthermore, the tampon according to the invention may comprise a narrowed and slightly rounded inserting end portion, although another embodiment is also possible, in which the inserting end portion of the tampon is widened, in particular mushroom-shaped or rivet-shaped. In such a case, all preferably extend along the majority of the length of the tampon.

Still further, the tampon according to the invention is available either as a digital tampon, namely a tampon, which is adapted for inserting by means of fingers on a single hand, or alternatively as an applicator tampon which is adapted to cooperate with appropriate applicator assembly.

Besides, a liquid permeable wrapper may be foreseen on the external surface of the tampon, which may extend over at least a portion of said external surface of the tampon.

On the other hand, the present invention also refers to an apparatus for manufacturing a tampon in accordance with the previously mentioned features, wherein such apparatus comprising a device, which is adapted for manufacturing of such tampon on the basis of pressing a corresponding blank in its radial direction towards the longitudinal axis thereof by means of four pairs of pressing jaws, which are equidistantly spaced apart from each other in the circumferential direction of said blank.

According to the invention, two pairs of jaws of appropriately pre-determined width B1 are adapted for pressing up to appropriately pre-determined depth T1 and are arranged in two planes, which extend perpendicularly with respect to each other and throughout the longitudinal axis of the blank, while the other two pairs of pressing jaws of appropriately pre-determined width B2 are adapted for pressing up to appropriately pre-determined depth T2 and are arranged in another two planes, which also extend perpendicularly with respect to each other and throughout the longitudinal axis of the blank, but are rotated for 45° around said longitudinal axis relatively to said planes of the previously mentioned pressing jaws, wherein each width B1, B2 of pressing jaws and each depth T1, T2 of pressing jaws is determined in such a manner that the shape of the silhouette or the cross-section of each obtained tampon essentially corresponds to a flattened circle or a rounded square having rounded corner areas, by which the distance between each two opposite corner areas on the external surface of the tampon is for approx. 10 to 35% greater than the distance between each two opposite lateral areas on the external surface of the tampon.

Apparatus according to the invention is designed in such a manner that each width B1, B2 of said pressing jaws and each depth T1, T2 of pressing by such jaws is determined in such a manner that either the following condition is fulfilled $T1 \neq T2$ and $B1 = B2$, or that $T1 \neq T2$ and $B1 > B2$, or optionally that $T1 \neq T2$ and $B1 < B2$.

The present invention further relates to a method of manufacturing a tampon in accordance with the previously described features. Such method generally comprising steps of
- preparing a tape-shaped mate consisting of fibrous material of each desired structure, which are compressed or concentrated in any other way into a desired form of vlies or a mate or any other non-woven fabric;
- winding up said band around the longitudinal axis by simultaneously inserting a string in order to obtain an approximately cylindrical blank;
- radial compression of said blank by means of a pressing device, which is adapted to form appropriate grooves on the circumferential surface of the blank in order to obtain a tampon.

In accordance with the present invention, the lastly mentioned step of compression of the blank into a tampon is performed by means of four pairs of pressing jaws, which are directed radially towards the longitudinal axis of the blank and are equidistantly spaced apart from each other around the circumference of said blank, where two pairs of pressing jaws having a pre-determined width B1 are intended for pressing up to a pre-determined depth T1 and are arranged in two planes, which extend perpendicularly with respect to each other and throughout the longitudinal axis of the blank, while the other two pairs of pressing jaws having a pre-determined width B are adapted for pressing up to a pre-determined depth T2 and are arranged in other two planes, which also extend perpendicularly with respect to each other and throughout the longitudinal axis of the blank, but are rotated for 45° around said longitudinal axis relatively to said planes of the previously mentioned pressing jaws, wherein each width B1, B2 of pressing jaws and each depth T1, T2 of pressing jaws is determined in such a manner that the shape of the silhouette or the cross-section of each obtained tampon essentially corresponds to a flattened circle or a rounded square having rounded corner areas, by which the distance A2 between each two opposite corner areas on the external surface of the tampon is for approx. 10 to 35% greater than the distance A1 between each two opposite lateral areas on the external surface of the tampon.

Said step of compression of the tampon in accordance with said method according to the invention is characterized in that each width B1, B2 of said pressing jaws and each depth T1, T2 of pressing by such jaws is determined in such a manner that either the following condition is fulfilled $T1 \neq T2$ and $B1 = B2$, or that $T1 \neq T2$ and $B1 > B2$, or optionally that $T1 \neq T2$ and $B1 < B2$.

Figure 4:
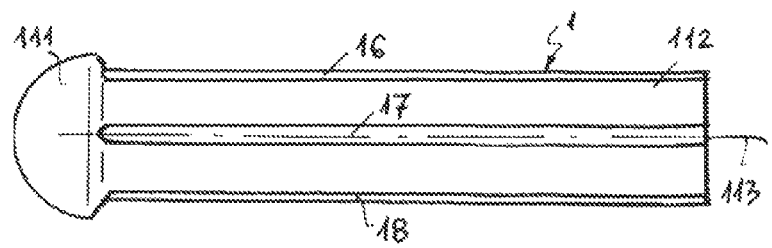
Figure 5:
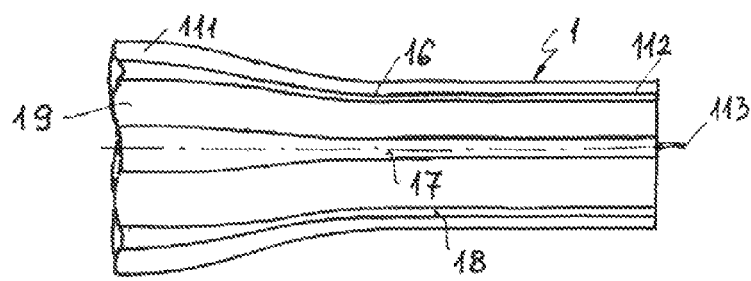
Figure 6:
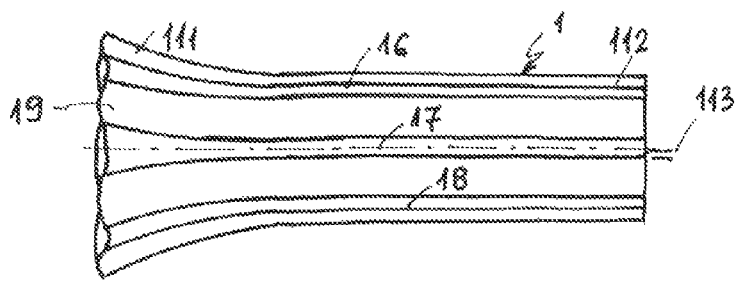

Now the invention will be described in more detail on the basis of embodiments, which are exclusively for illustrative purposes and without limitation with respect to the scope of the invention shown in the enclosed drawings, wherein FIG. 1 is a schematically shown perspective view of an idealized tampon according to the invention;

FIG. 2 is also a schematically shown top view of a device for manufacturing tampons according to the invention, observed in the axial direction of tampon;

FIG. 3 is a top view of a further embodiment of the tampon according the invention;

FIG. 4 is a top view of a still further embodiment of the tampon according the invention;

FIG. 5 shows a tampon according to FIG. 1 upon being exposed to the moisture in the area of its end portion;

FIG. 6 shows an analogous digital tampon according to prior art, also upon being exposed to the moisture in the area of its end portion.

Figure 7:
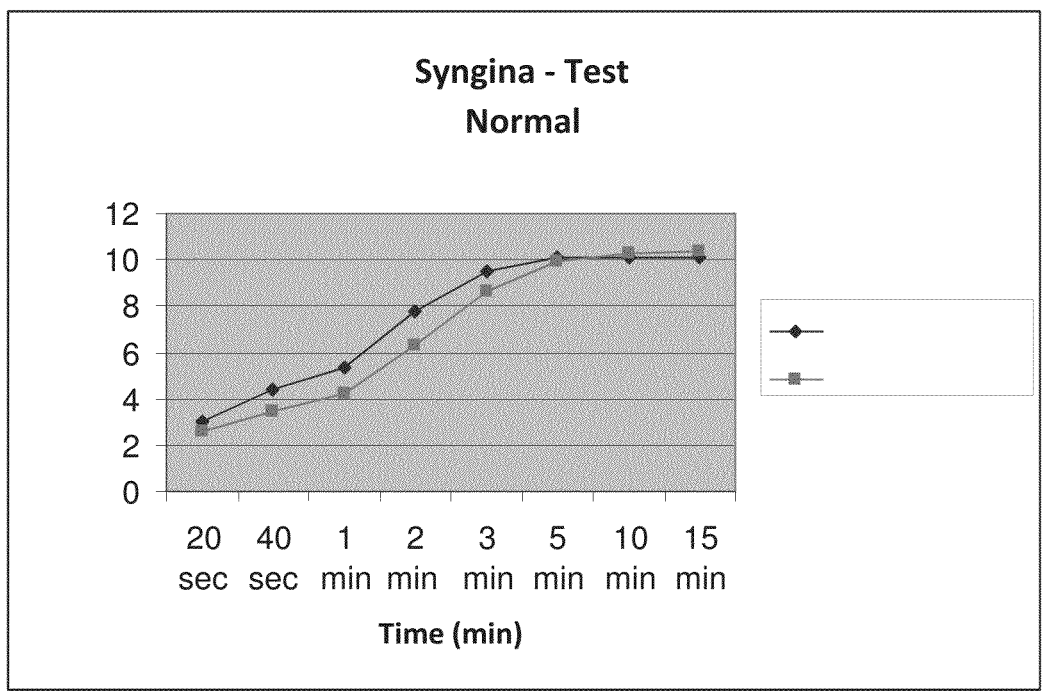
FIG. 7 is a diagram illustrating absorption over time for a test tampon.

FIG. 7 shows a diagram illustrating absorption over time for a test tampon.

Tampon 1 according to the invention consists of absorptive non-woven fibrous material, preferably on the basis of natural fibers e.g. of cellulose, or optionally of a combination of natural and synthetic fibers. Tampon 1 is formed symmetrically with respect to its longitudinal axis 100 and—when bearing in mind the direction of inserting thereof—comprises a forward portion, namely an inserting portion 111, as well as a rearward portion 112, in the area of which the tampon 1 is furnished with a cord 113.

A silhouette or a transversal cross-section of the tampon according to the invention is flattened along two planes, which are perpendicular to each other, and essentially corresponds to a flattened circle or to a square having rounded corner areas. Eight grooves 11, 12, 13, 14 15, 16, 17, 18 are formed on the external surface of the tampon 1, which are in the circumferential direction equally spaced apart from each other and are in the longitudinal direction of the tampon 1 extending parallel to the longitudinal axis 100 of the tampon 1. Said grooves 11, 12, 13, 14 15, 16, 17, 18 generally extend along at least a part of the complete length L of the tampon 1. Regarding the tampon according to FIG. 1, said grooves 11, 12, 13, 14 15, 16, 17, 18 extend over the complete length L of the tampon 1, while in other possible embodiments, e.g. in those according to FIGS. 3 and 4, may extend just along certain portion of the tampon 1 length L.

Said grooves 11, 12, 13, 14 15, 16, 17, 18 are preferably formed in such a way that four grooves 11, 13, 15, 17, which are located in two planes, which are oriented perpendicular with respect to each other and extend throughout the longitudinal axis 100, are formed in at least approximately in same dimensions, and are preferably identical, at least regarding the width B1 and the depth T1 thereof. The other four grooves 12, 14, 16, 18, which are located in other two planes, which are also perpendicular with respect to each other and extend throughout the longitudinal axis 100 of the tampon, and are moreover rotated for 45° around said axis 100 relatively to previously mentioned planes, are also formed in at least approximately similar, preferably identical, dimensions at least with respect to the width B2 and the depth T2 thereof, wherein these dimensions B2, T2 are different with respect to dimensions of the previously mentioned grooves 11, 13, 15, 17.

Regarding the shown embodiment, the grooves 11, 13, 15, 17 having the width B1 and the depth T1 are pressed on the external surface of the tampon 1, and also the grooves 12, 14, 16, 18 having the width B2 and the depth T2. Each groove 11, 13, 15, 16 having the width B1 and the depth T1 is located between two neighboring grooves 12, 14, 16, 18 having the width B2 and the depth T2, or vice versa.

Those skilled in the art should understand that an idealized shape of the silhouette or the cross-section is shown in FIG. 1, which is determined by the shape of pressing jaws 21, 22, 23, 24, 25, 26, 27, 28 of the pressing device 20 (FIG. 2). Actual dimensions of grooves 11, 12, 13, 14 15, 16, 17, 18 may generally depend on at least certain parameters, e.g. on each structure of fibers of a blank 10, on pressure achieved by pressing jaws 21, 22, 23, 24, 25, 26, 27, 28 and also on dimensions B1, T1; B2, T2 of the pressing jaws 21, 22, 23, 24, 25, 26, 27, 28 in each pressing device 20.

Moreover, a rib 19 is available between each two neighboring grooves 11, 12, 13, 14, 15, 16, 17, 18 of the tampon 1 according to the invention, and its external surface together with the external surface of each opposite rib 19 regarding the silhouette or the cross-section of the tampon 1 defines the overall dimension A1, A2 in the transversal direction of the tampon 1, whilst the bottom surfaces of the grooves 11, 12, 13, 14, 15, 16, 17, 18 define a correspondingly compressed core of the tampon 1 consisting of absorbent fibrous material.

When bearing in mind that said grooves 11, 12, 13, 14, 15, 16, 17, 18 are formed by means of radial pressing of the blank 10 into corresponding shape of the tampon 1, each available cross-section of the tampon 1 is then not e.g. of essentially circular shape but is thanks to the presence of said grooves 11, 12, 13, 14, 15, 16, 17, 18 in two pairs of mutually rectangular and correspondingly pivoted pairs of planes available in the shape of a square having rounded corner areas (FIG. 1), wherein such square having rounded corner areas is then defined by means of thickness A1 between each opposite lateral surfaces as well as of diagonal distance between each two opposite rounded corner areas.

The dimensions of the silhouette or the transversal cross-section of the tampon 1, namely the width B1, B2 and the depth T1, T1 of grooves 11, 12, 13, 14, 15, 16, 17, 18, are preferably determined in such a way that the diagonal distance A2 is for approx. 10 to 35% greater than the thickness A1 of the tampon 1.

Those skilled in the art are aware of the presence of various embodiments of tampons on the market, which may however with respect to quite physiologic requirements regarding the target users be arranged into three main groups. The average size of tampons is normally designated as "normal", by which such "normal" class is then defined by appropriate range of diameters and the length L of the tampon 1.

The tampon 1 according to the invention is formed in such a way that either its thickness A1 or its diagonal size A2 corresponds to the common size of the diameter of such tampons. The first one of both these possibilities is however preferred and may also easily be compared with the prior art, since the quantity of each available absorbent fibrous material is then essentially the same or very similar as in a common cylindrical tampon 1 in the class "normal". On the other hand, appropriately modified silhouette and cross section of the tampon according to the invention excels in correspondingly greater cross-section surface with regard to the cylindrical tampon 1 according to prior art, providing that both of them are consisting of the same quantity of the absorbent fibrous material, and moreover, the moment of inertia of such cross-section is also enhanced, which obviously leads to increasing of stability, namely increasing of stiffness of tampon when being bent or exposed to buckling.

A further embodiment of the tampon 1 according to the invention is shown in FIG. 3, wherein the inserting end portion 111 is slightly rounded in order to enable easily inserting.

A still further embodiment of the tampon 1 according to the invention is shown in FIG. 4, wherein the inserting end portion 111 is bulked, by which such tampon 1 may then be used in appropriate applicator.

In both these lastly mentioned embodiments, the grooves 11, 12, 13, 14, 15, 16, 17, 18 extend along the majority of the length L of the tampon 1.

Besides, the tampon 1 may be furnished with a liquid permeable wrapper, which may extend along the complete external surface of the tampon or along at least a portion thereof.

The inserting end portion of the tampon 1 according to the invention, which is shown in FIG. 5, is exposed to the same quantity of liquid as the tampon 1 according to prior art, which is shown in FIG. 6. When exposed to the moisture, the tampon 1 according to the invention is expanded and becomes bulky like any other tampon. However, expanding of tampon 1 according to the invention occurs gradually, by which the external surfaces is transformed into a bat-like shape. On the contrary, the comparative digital tampon 1 according to the prior art (like e.g. a tampon according to EP 0 422 660) having the same length L and consisting of equal amount of the fibrous material is expanded essentially quicker, by which its external surface is transformed into a trumpet-like shape. Consequently, the sealing capability of the tampon 1 according to the invention is essentially improved, and the possibility of any leakage of the fluid, which has been absorbed by the tampon 1, is correspondingly reduced.

Example

Benefits of the tampon 1 within the scope of the present invention may also be presented on the basis of results obtained by measuring the most important characteristics, which are shown in Table 1 and 2 below.

Regarding Table 1, the data illustrate comparing relevant characteristics of a classic tampon, named as "Tampon 8+0", of average size "Normal", with a tampon according to the invention having the same size and consisting of the same material, which is in said Table named as "Tampon 4+4". Said "Tampon 8+0" comprises eight ribs and grooves available on the external surface thereof, and having the outer diameter of approx. 12.5 mm, while the weight of the dry tampon is approx. 2.5 g. The tampon according to the invention (i.e. "Tampon 4+4") is furnished with two pairs of grooves 11, 13, 15, 17 of greater depth and two pairs of grooves 12, 14, 16, 18 of smaller depth, but the weight and overall size thereof essentially correspond to the previously mentioned classic tampon (i.e. "Tampon 8'0"). On the other hand, the data in the Table 2 illustrate comparison of characteristics of some greater tampons 1, namely of "Tampon 8+1" and Tampon 4+4", which belong to the group "Super", by which the outer diameter of such tampon 1 without packaging wrapper is approx. 14.5 mm, and the weight of a dry tampon 1 is approx. 3.2 g.

TABLE 1

| Analysis: | Normal 8 + 0 | Normal 4 + 4 |
|---|---|---|
| Tampon weight (g): without wrapper | 2.6 | 2.5 |
| Diameter (mm): without wrapper | 12.4 | 12.5 |
| Syngina (g): | | |
| after 20 s | 2.4 | 2.6 |
| after 3 min | 9.6 | 8.9 |
| after 15 min | 10.1 | 9.2 |
| BE absorption (g) | 14.3 | 14.6 |
| EDANA (g): | 10.4 | 10.4 |
| Capacity (g/g): | 3.9 | 4.0 |
| Stability (N): | 41.7 | 48 |

TABLE 2

| Analysis: | Super 8 + 0 | Super 4 + 4 |
|---|---|---|
| Tampon weight (g): without wrapper | 3.2 | 3.2 |
| Diameter (mm): without wrapper | 14.5 | 14.5 |
| Syngina (g): | | |
| after 20 s | 3.6 | 3.5 |
| after 3 min | 11.5 | 11.7 |
| after 15 min | 12.1 | 12.0 |
| BE absorption (g) | 17.8 | 17.9 |
| EDANA (g): | 12.9 | 13.3 |
| Capacity (g/g): | 4.0 | 4.2 |
| Stability (N): | 35.1 | 36 |

Concerning both tables, the tampon weight (given in gram) means the weight of a compressed fibrous material in a dry (non-used) tampon prior to inserting into corresponding packaging or immediately upon removal said packaging i.e. said wrapper. The diameter of tampon is a maximum outer diameter of the tampon in the area of ribs 19.

The term "Syngina" means experimental value of the liquid, which is absorbed by the tampon when exposed to moisture on the one end portion within a pre-determined time, and which is then measured and expressed in grams. This is a commonly recognized professional examination and there is no need to express in more detail all prescribed conditions and requirements, which must be taken into account during execution thereof. In general, kinetic of absorbing the liquid is observed at the body temperature 37° C. and by simultaneously simulating of the vaginal pressure. The tampon 1 is exposed to the liquid, which is a so called "artificial blood" (German abbreviation is BE and English abbreviation is SB). Values in Table 1 and 2 refer to each quantity of such artificial blood after a pre-determined time period, and also maximum values, which are absorbed by each tampon 1 up to the moment, when the leakage occurs.

On the other hand, the term "EDANA" means a static examination of absorptiveness of the tampon 1, in which the end portion 111 of each tampon 1 is permanently and with constant velocity supplied by the liquid unless the tampon 1 becomes completely saturated. As soon as the maximum absorption is achieved and the leakage of the tampon 1 occurs, the amount of the absorbed liquid is measured and expressed per weight of the tampon 1 in grams, and such specific absorption is presented in the Table 1 and 2 as the "Capacity (g/g)". The liquid has been 1% solution of NaCl in water, and the measuring has been performed at 27° C.

The term "stability" in Table 1 and 2 refers to examining a tampon with regard to strength thereof when exposed to pressure and buckling in its longitudinal i.e. axial direction, by which the values in Table 1 and 2 mean each force (expressed in N), which results in buckling or destruction of the tampon.

As evident from results given in the Table 1 and 2, stability of the tampon according to the invention ("Tampon 4+4") is at least such and mostly greater than stability of the classic tampon ("Tampon 8+0"). Significant benefits of the tampon 1 according to the invention also result from the kinetics of absorption during a pre-determined time period. Just for illustrative purposes, such kinetics is also graphically presented in the Diagram illustrated in FIG. 7, but only for "Normal" size of the tampon 1.

As evident in the Diagram illustrated in FIG. 7, during the early phase of using the tampon 1 according to the invention ("Tampon 4+4"; size "Normal"), absorption is relatively low, but is then intensively increasing towards the end period of the use, so that the specific absorptiveness (g/g) of such used tampon 1 reaches the specific absorptiveness (g/g) of the known tampon. The reason for that has already been explained in relationship with the phenomena, which is shown in FIGS. 5 and 6.

A device 20 for manufacturing of tampons 1 according to the invention comprises four pairs of pressing jaws 21, 22, 23, 24, 25, 26, 27, 28, which are equidistantly arranged around the circumference of a blank 10, wherein two pairs of jaws 21, 23, 25, 27 having the width B1 and being adapted for pressing up to the depth T1 are arranged in two planes, which extend perpendicularly with respect to each other and throughout the longitudinal axis 100 of the blank 10, while the other two pairs of jaws 22, 24, 26, 28 having the width B2 and being adapted for pressing up to the depth T2 are arranged in other two planes, which also extend perpendicularly with respect to each other and throughout the longitudinal axis 100 of the blank 10, but are rotated for 45° around said longitudinal axis 100 with respect to said planes of the previously mentioned pressing jaws 21, 23, 25, 27. Accordingly, two pairs of jaws 21, 23, 25, 27 having the width B1 are intended for pressing up to the depth T1 and are arranged in two planes, which extend perpendicularly with respect to each other and throughout the longitudinal axis 100 of the blank 10, while the other two pairs of jaws 22, 24, 26, 28 having the width B2 are adapted for pressing up to the depth T2 and are arranged in other two planes, which also extend perpendicularly with respect to each other and throughout the longitudinal axis 100 of the blank 10, but are rotated for 45° around said longitudinal axis 100 relatively to said planes of the previously mentioned pressing jaws 21, 23, 25, 27. Moreover, each width B1, B2 and each depth T1, T2 of pressing by jaws is determined in such a manner that the condition T1≠T2 is fulfilled when either B1=B2 or when B1<B2 or even when B1>B2.

Such tampon 1 is made by process, which is performed by means of the device according to FIG. 1, and which includes steps of
preparing a tape-shaped mate consisting of fibrous material of a previously mentioned structure, which are compressed or concentrated in any other way into a desired form like mate or vlies or any other non-woven fabric;

winding up said tape-shaped mate around the longitudinal axis 100 by simultaneously inserting a string 13 in order to obtain an approximately cylindrical blank 10;

compression of said blank 10 by means of a pressing device 20 comprising four pairs of pressing jaws 21, 22, 23, 24, 25, 26, 27, 28, which extend radially towards the longitudinal axis 100 of the blank and are arranged equidistantly spaced apart from each other around the circumference of the blank 10, wherein two pairs of jaws 21, 23, 25, 27 having the width B1 are intended for pressing up to the depth T1 and are arranged in two planes, which extend perpendicularly with respect to each other and throughout the longitudinal axis 100 of the blank 10, while the other two pairs of jaws 22, 24, 26, 28 having the width B2 are adapted for pressing up to the depth T2 and are arranged in other two planes, which also extend perpendicularly with respect to each other and throughout the longitudinal axis 100 of the blank 10, but are rotated for 45° around said longitudinal axis 100 relatively to said planes of the previously mentioned pressing jaws 21, 23, 25, 27. In this, each width B1, B2 and each depth T1, T2 of pressing by jaws is determined in such a manner that the condition T1≠T2 is fulfilled when either B1=B2 or when B1<B2 or when B1>B2.

The invention claimed is:

1. A tampon, comprising:
an elongated tampon blank having a longitudinal axis, a length along the longitudinal axis, and an outer surface along the length that includes a circumference;
a first set of grooves that are each defined by the elongated tampon blank subsequent to the manufacture of the tampon, that each extend along the entirety of the length of the elongated tampon blank and into the elongated tampon blank a first depth from the outer surface, and that are equally spaced apart from each other about the circumference of the elongated tampon blank; and
a second set of grooves that are each defined by the elongated tampon blank subsequent to the manufacture of the tampon, that each extend along at least a majority of the length of the elongated tampon blank and into the elongated tampon blank a second depth from the outer surface that is less than the first depth, and that are equally spaced apart from each other about the circumference of the elongated tampon blank.

2. The tampon of claim 1, wherein each of the second set of grooves are spaced part about the circumference of the elongated tampon blank from adjacent ones of the first set of grooves by a 45 degree arc.

3. The tampon of claim 1, wherein the elongated tampon blank includes an absorbent, non-woven, fibrous material.

4. The tampon of claim 1, wherein the outer surface of the elongated tampon blank includes a first pair of sides that are parallel to each other, a second pair of sides that are parallel to each other and that are perpendicular to the first pair of sides, and a plurality of rounded corners that each extend between any two of the sides and that each define at least a portion of one of the second set of grooves.

5. The tampon of claim 2, wherein a first distance between any two of the plurality of the rounded corners that are opposite the elongated tampon blank from each other is 10-35% greater than a second distance between any two of the plurality of rounded corners that are adjacent each other on the elongated tampon blank.

6. The tampon of claim 1, wherein the first set of grooves each include a first width, and wherein the second set of grooves each include a second width that is less than the first width.

7. The tampon of claim 1, wherein the first set of grooves each include a first width, and wherein the second set of grooves each include a second width that is greater than or equal to the first width.

8. The tampon of claim 1, wherein the second set of grooves each extend along the entirety of the length of the elongated tampon blank.

9. The tampon of claim 1, further comprising:
an inserting end portion on an end of the elongated tampon base, wherein the inserting end portion is rounded.

10. The tampon of claim 1, further comprising:
a string extending from an end of the elongated tampon base.

11. The tampon of claim 1, wherein the tampon is a digital tampon that is configured to be inserted using fingers on a hand.

12. The tampon of claim 1, further comprising:
an applicator assembly that is configured for inserting the tampon.

13. A tampon manufacturing system, comprising:
a pressing device that is configured to accept an elongated tampon blank having a longitudinal axis, a length along the longitudinal axis, and an outer surface along the length;
a first set of pressing jaws on the pressing device that include a first pair of pressing jaws that are oriented on a first plane and that are configured to press a first pair of grooves into the elongated tampon blank, and a second pair of pressing jaws that are oriented on a second plane that is perpendicular to the first plane and that are configured to press a second pair of grooves into the elongated tampon blank, wherein subsequent to the manufacture of a tampon using the pressing device, the first pair of grooves and the second pair of grooves each extend along the entirety of the length of the elongated tampon blank and into the elongated tampon blank a first depth from the outer surface; and
a second set of pressing jaws on the pressing device that include a third pair of pressing jaws that are oriented on a third plane and that are configured to press a third pair of grooves into the elongated tampon blank, and a fourth pair of pressing jaws that are oriented on a fourth plane that is perpendicular to the third plane and that are configured to press a third pair of grooves into the elongated tampon blank, wherein subsequent to the manufacture of a tampon using the pressing device, the third pair of grooves and the fourth pair of grooves each extend along a majority of the length of the elongated tampon blank and into the elongated tampon blank a second depth from the outer surface that is less than the first depth.

14. The tampon manufacturing system of claim 13, wherein the first set of pressing jaws are configured to press the first pair of grooves into the elongated tampon blank that include a first width, the second set of pressing jaws are configured to press the second pair of grooves into the elongated tampon blank that include the first width, the third set of pressing jaws are configured to press the third pair of grooves into the elongated tampon blank that include a second width that is less than the first width, and the fourth set of pressing jaws are configured to press the fourth pair of grooves into the elongated tampon blank that include the second width.

15. The tampon manufacturing system of claim 13, wherein the first set of pressing jaws are configured to press the first pair of grooves into the elongated tampon blank that include a first width, the second set of pressing jaws are configured to press the second pair of grooves into the elongated tampon blank that include the first width, the third set of pressing jaws are configured to press the third pair of grooves into the elongated tampon blank that include a second width that is greater than or equal to the first width, and the fourth set of pressing jaws are configured to press the fourth pair of grooves into the elongated tampon blank that include the second width.

16. The tampon manufacturing system of claim 13, wherein each of the third plane and the fourth plane are spaced apart from the first plane and the second plane by a 45 degree arc.

17. A method for manufacturing a tampon, comprising:
positioning an elongated tampon blank in a pressing device, wherein the elongated tampon blank includes a longitudinal axis, a length along the longitudinal axis, and an outer surface along the length;
pressing, using a first pair of pressing jaws on the pressing device that are oriented on a first plane, a first pair of grooves into the elongated tampon blank such that, subsequent to the manufacture of a tampon using the pressing device, the first pair of grooves each extend along the entirety of the length of the elongated tampon blank and into the elongated tampon blank a first depth from the outer surface;
pressing, using a second pair of pressing jaws on the pressing device that are oriented on a second plane that is perpendicular to the first plane, a second pair of grooves into the elongated tampon blank such that, subsequent to the manufacture of a tampon using the pressing device, the second pair of grooves each extend along the entirety of the length of the elongated tampon blank and into the elongated tampon blank the first depth from the outer surface;
pressing, using a third pair of pressing jaws on the pressing device that are oriented on a third plane, a third pair of grooves into the elongated tampon blank such that, subsequent to the manufacture of a tampon using the pressing device, the third pair of grooves each extend along a majority of the length of the elongated tampon blank and into the elongated tampon blank a second depth from the outer surface that is less than the first depth; and
pressing, using a fourth pair of pressing jaws on the pressing device that are oriented on a fourth plane that is perpendicular to the third plane, a fourth pair of grooves into the elongated tampon blank such that, subsequent to the manufacture of a tampon using the pressing device, the fourth pair of grooves each extend along a majority of the length of the elongated tampon blank and into the elongated tampon blank the second depth from the outer surface.

18. The method of claim 17, wherein the first pair of grooves include a first width, the second pair of grooves include the first width, the third pair of grooves include a second width that is less than the first width, and the fourth pair of grooves include the second width.

19. The method of claim 17, wherein the first pair of grooves include a first width, the second pair of grooves include the first width, the third pair of grooves include a second width that is greater than or equal to than the first width, and the fourth pair of grooves include the second width.

20. The method of claim 17, wherein each of the third plane and the fourth plane are spaced apart from the first plane and the second plane by a 45 degree arc.

* * * * *